(12) United States Patent
Lee et al.

(10) Patent No.: US 7,038,218 B2
(45) Date of Patent: May 2, 2006

(54) INSPECTION BY A TRANSMISSION ELECTRON MICROSCOPE OF A SAMPLE

(75) Inventors: Myoung-Rack Lee, Suwon-si (KR); Sun-Young Lee, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 10/974,953

(22) Filed: Oct. 28, 2004

(65) Prior Publication Data

US 2005/0087697 A1    Apr. 28, 2005

(30) Foreign Application Priority Data

Oct. 28, 2003   (KR) ..................... 10-2003-0075553

(51) Int. Cl.
*H01J 37/20* (2006.01)
*G01N 1/28* (2006.01)
(52) U.S. Cl. ................. 250/440.11; 250/304; 250/307; 250/311; 451/41; 451/364
(58) Field of Classification Search ..................... None
See application file for complete search history.

(56) References Cited

U.S. PATENT DOCUMENTS

| | | | | | |
|---|---|---|---|---|---|
| 5,472,566 | A | * | 12/1995 | Swann et al. | 204/192.34 |
| 5,791,973 | A | * | 8/1998 | Nishio | 451/41 |
| 6,005,248 | A | * | 12/1999 | Mori et al. | 250/311 |

* cited by examiner

*Primary Examiner*—Jack I. Berman
(74) *Attorney, Agent, or Firm*—Volentine Francos & Whitt, PLLC

(57) ABSTRACT

A method of manufacturing a transmission electron microscope inspection sample. The sample is mounted into a recess in the mount and the sample is grinded to a preset target thickness. A recess for mounting the sample and a groove for separating the sample from the recess are formed on a top surface of the mount. The sample is fixed into the recess using mounting wax. The protruding portion of the sample protrudes above the mount and is grinded by the grinder. The depth of the recess is based on the target thickness of the sample. The protruding portion of the sample is grinded to the top surface of the mount.

19 Claims, 5 Drawing Sheets

INSPECTION BY A TRANSMISSION ELECTRON MICROSCOPE OF A SAMPLE

BACKGROUND OF THE INVENTION

1. Field of the Invention

Embodiments of the present invention relate to a mount for mounting a transmission electron microscope inspection sample. Priority is claimed from Korean Patent Application No. 2003-75553, filed on Oct. 28, 2003, the contents of which are herein incorporated by reference in its entirety.

2. Description of the Related Art

A semiconductor device may be manufactured to form an electric circuit on a semiconductor substrate. A packaging process may separate the semiconductor substrate into individual semiconductor chips and seal each of the exposed semiconductor chips using an epoxy resin. The manufacturing process may include the following: A deposition process for forming a thin layer on the semiconductor substrate. A CMP process for chemically and mechanically polishing the thin layer. A photolithography process for forming a photoresist pattern on the thin layer. An etching process for etching the thin layer into an electrical pattern using the photoresist pattern as a mask. An ion implantation process for implanting ions into a predetermined region of the semiconductor substrate. A cleaning process for cleaning impurities from the semiconductor substrate. An inspection process for inspecting a surface of the semiconductor substrate to detect defects in the thin layer or pattern.

Various kinds of inspection devices (e.g. a scanning electron microscope (SEM), a transmission electron microscope (TEM), and a secondary ion mass spectrometer (SIMS)) are used in the inspection process. The TEM uses an electron beam which passes through a sample. The sample may have a thickness less than or equal to about 70 μm. The sample may be mounted on a top surface of a cylindrical mount using mounting wax. A rear surface of the sample may be grinded using a grinder, so that the sample has a thickness of about 70 μm.

While grinding the rear surface of the sample, it is difficult to measure the thickness of the sample. If the thickness of the sample is measured with poor accuracy, the sample is easily broken during the grinding of the sample. Further, it may be difficult to accurately grind the sample to a target thickness.

SUMMARY OF THE INVENTION

Embodiments of the present invention relate to a mount which mounts a sample for inspection, such that the sample is grinded to a target thickness. Embodiments of the present invention relate to a method of manufacturing a sample for inspection by a TEM, using a mount.

Embodiments of the present invention relate to a grinding mount for receiving a transmission electron microscope (TEM) inspection sample to be grinded. The sample has a thickness and a given outer profile. The grinding mount has a rigid body having a principle surface. The grinding mount has a recess defined in the principle surface of the rigid body. The horizontal profile of the recess corresponds to the given outer profile of the sample. The vertical depth of the recess is less than the given thickness of the sample. The grinding mount includes a groove defined in the principle surface of the rigid body. The groove partially overlaps the recess. The vertical depth of the groove is greater than the vertical depth of the recess.

Embodiments of the present invention relate to a method of treating a transmission electron microscope inspection sample. The method includes mounting the sample to the recess in a mount. The shape of the recess corresponds to the shape of the sample. The method includes grinding a protruding portion of the sample which protrudes from the mount. The method includes separating the sample from the mount.

BRIEF DESCRIPTION OF THE DRAWINGS

The above and other features and advantages of embodiments of the present invention will become readily apparent by reference to the following detailed description when considered in conjunction with the accompanying drawings, in which.

DESCRIPTION OF THE EXEMPALRY EMBODIMENTS

The present invention now will be described more fully hereinafter with reference to the accompanying drawings, in which example embodiments of the present invention are illustrated.

Figure 1:
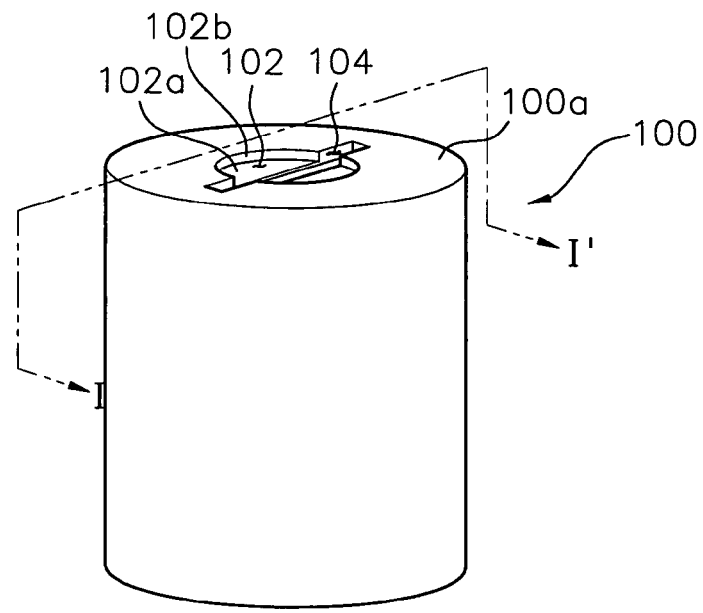
FIG. 1 is a perspective view illustrating a mount for mounting a transmission electron microscope inspection sample, according to example embodiments of the present invention.
Figure 2:
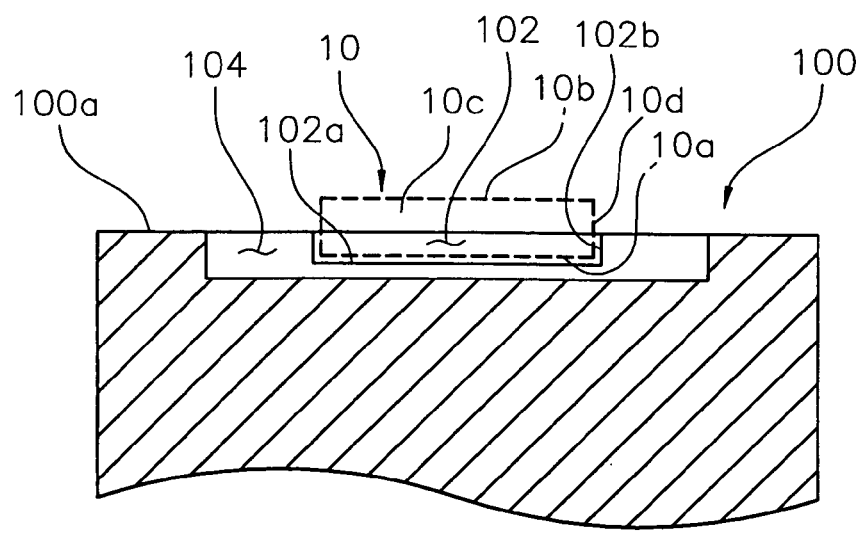
FIG. 2 is a cross sectional view taken along the line I–I' of FIG. 1.

FIG. 1 is a perspective view illustrating a mount which mounts a transmission electron microscope inspection sample, according to embodiments of the present invention. FIG. 2 is a cross sectional view taken along the line I–I' of FIG. 1.

Referring to FIGS. 1 and 2, a mount 100, according to embodiments of the present invention, has a cylindrical shape, a recess 102, and a groove 104. The recess 102 mounts a circular sample 10. The groove 104 separates the sample 10 from the recess 102. The recess 102 and the groove 104 are formed on a top surface 100a of the mount 100. In embodiments, the mount 100 is made of stainless steel. The recess 102 may be formed in a circular shape. Although example embodiments include a circular recess, any other shape (e.g. a rectangle) could be utilized as the shape of the recess, in accordance with the shape of the sample, as would be appreciated by one of ordinary skill in the art.

In embodiments of the present invention, the diameter of the sample 10 is about 3 mm and the diameter of the recess 102 is in a range from about 3.05 mm to about 3.15 mm. In example embodiments, the recess shown in FIGS. 1 and 2 has a diameter of about 3.1 mm. An actual thickness of the circular sample 10 is about 400 μm, and a target thickness of the sample 10 is preset to about 70 μm, in accordance with example embodiments. The depth of the recess 102 may be greater than the target thickness of the sample (e.g. by about 1 μm to about 10 μm). For example, the depth of the recess 102 may be in the range of about 71 μm to about 80 μm, while the depth of the recess 102 shown in FIGS. 1 and 2 may be about 75 μm.

Mounting wax (not shown) may be interposed between the recess 102 and the sample 10, so that the sample 10 is firmly mounted into the recess 102. The sample 10 is inserted into the recess 102 such that the front surface 10*a* of the sample 10 faces the bottom surface 102*a* of the recess 102. Since the circular sample 10 is mounted into recess 102 using the mounting wax, the recess 102 has the depth greater than the target thickness of the sample 10. For example, the mounting wax coated on the bottom surface 102*a* of the recess 102 has a thickness in the range of about 1 μm to about 10 μm.

After mounting the circular sample 10 into the recess 102 in the mount 100, the exposed rear surface 10*b* of the sample 10 is grinded by a grinder (not shown). A protruding portion 10*c* of the sample 10 that protrudes above the top surface 100*a* of the mount 100 is grinded to approximately the same level as the top surface 100*a*. Accordingly, the sample 10, having a circular shape, may be manufactured to a target thickness. In addition, while the sample 10 is grinded, the mounting wax is interposed between a side surface 10*d* of the sample 10 and the recess 102, preventing the sample 10 from breaking.

The groove 104 extends in a radial direction from the recess 102, and overlaps a side surface 102*b* of the recess 102. The groove 104 has a width smaller than the radius of the recess 102, a length longer than a diameter of the recess 102 and a depth deeper than the depth of the recess 102. The groove 104 can be used to separate the sample 10 from the recess 102 and preferably has a depth in the range of about 80 μm to about 90 μm. For example, the groove 104 shown in FIGS. 1 and 2 may have a width of about 1 mm, a length of about 6 mm, and a depth of about 85 μm.

After grinding the sample 10, the mounting wax interposed between the sample 10 and the recess 102 is heated to a temperature of about 100° C. to be softened. Then, the sample 10 (e.g. having a circular shape) is separated from the recess 102 using the groove 104. If the mounting wax is dissolvable in acetone, the sample 10 may be separated from the recess 102 using acetone.

Figure 3:
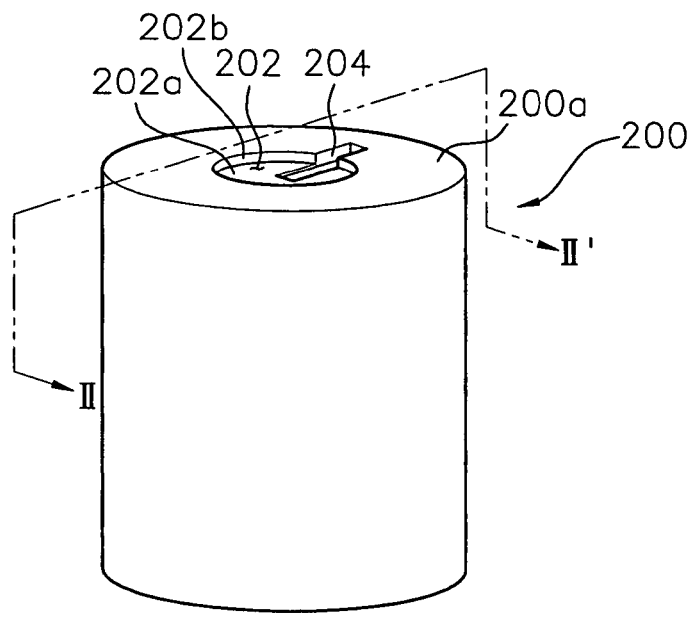
FIG. 3 is a perspective view illustrating a mount for mounting a transmission electron microscope inspection sample, according to example embodiments of the present invention.
Figure 4:
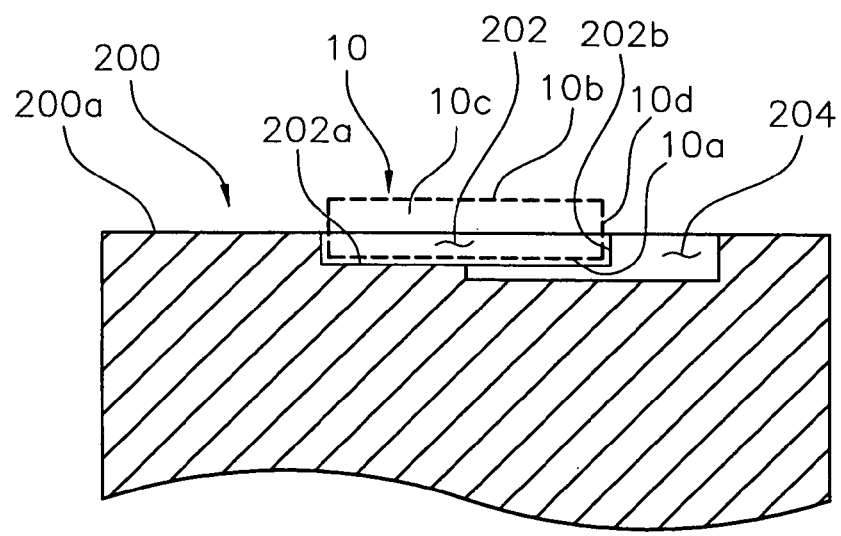
FIG. 4 is a cross sectional view taken along the line II–II' of FIG. 3.

FIG. 3 is a perspective view illustrating a mount for mounting a transmission electron microscope inspection sample, according to embodiments of the present invention. FIG. 4 is a cross sectional view taken along the line II–II' of FIG. 3. Referring to FIGS. 3 and 4, a mount 200, according to example embodiments of the present invention, has a cylindrical shape, a recess 202 for mounting a circular sample 10, and a groove 204 for separating the sample 10 from the recess 202. The recess 202 and groove 204 are formed on a top surface 200*a* of the mount 200. The recess 202 has a shape corresponding to the shape of the sample 10.

The groove 204 extends in a radial direction of the recess 202 and overlaps a side surface 202*b* of the recess 202. The groove 204 has a width smaller than the radius of the recess 202, a length longer than the radius of the recess 202, and a depth greater than the depth of the recess 202. The groove 204 can be used to separate the sample 10 from the recess 202. The groove 204 may have a depth in a range of about 80 μm to about 90 μm. For example, the groove 204 shown in FIGS. 3 and 4 may have a width of about 1 mm, a length of about 6 mm, and a depth of about 85 μm. Reference numerals 202*a* and 202*b* denote a bottom surface and a side surface of the recess 202, respectively.

Figure 5A:
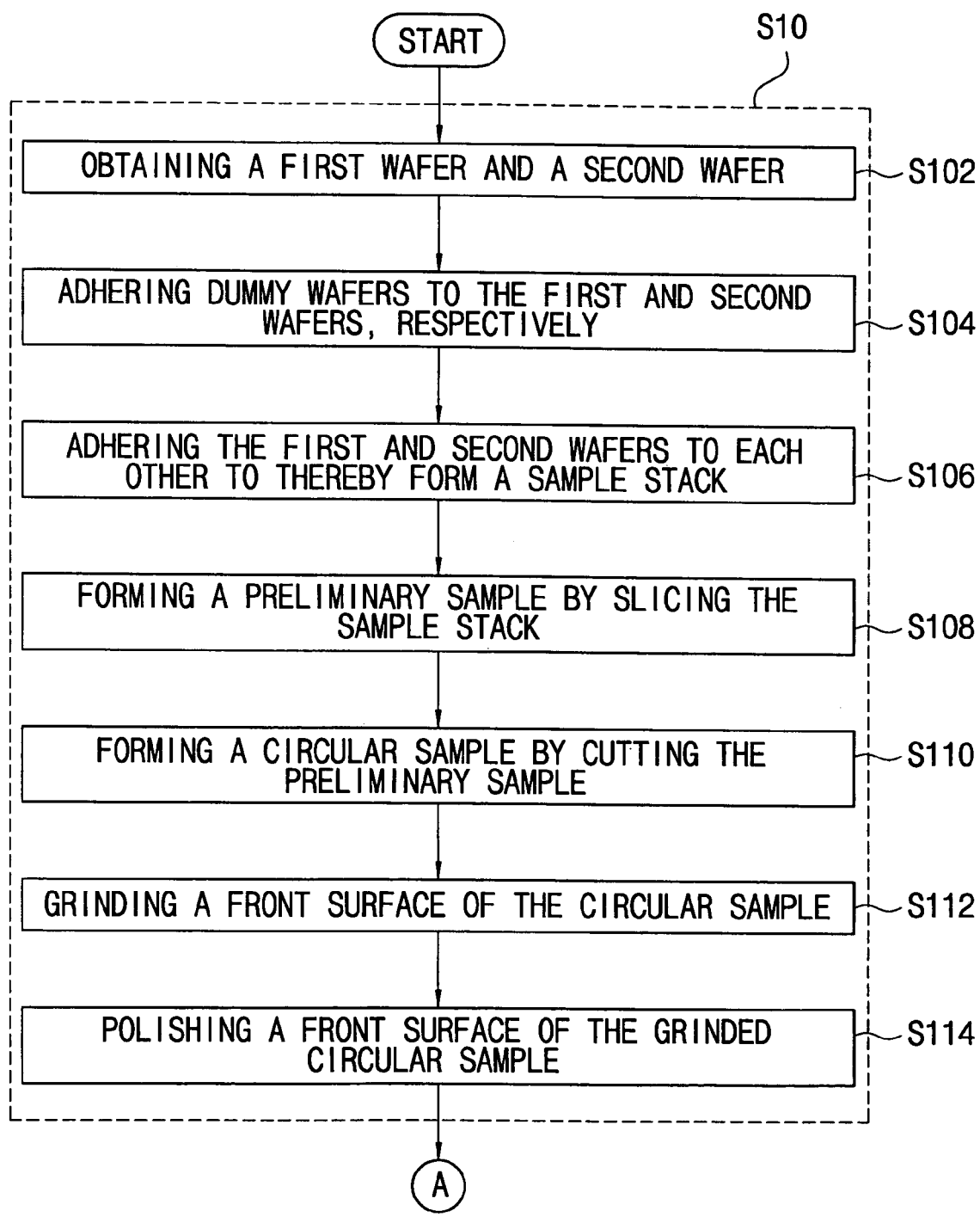
FIGS. 5A and 5B are flow charts illustrating a method of manufacturing a transmission electron microscope inspection sample, using the mount shown in FIG. 1.
Figure 5B:
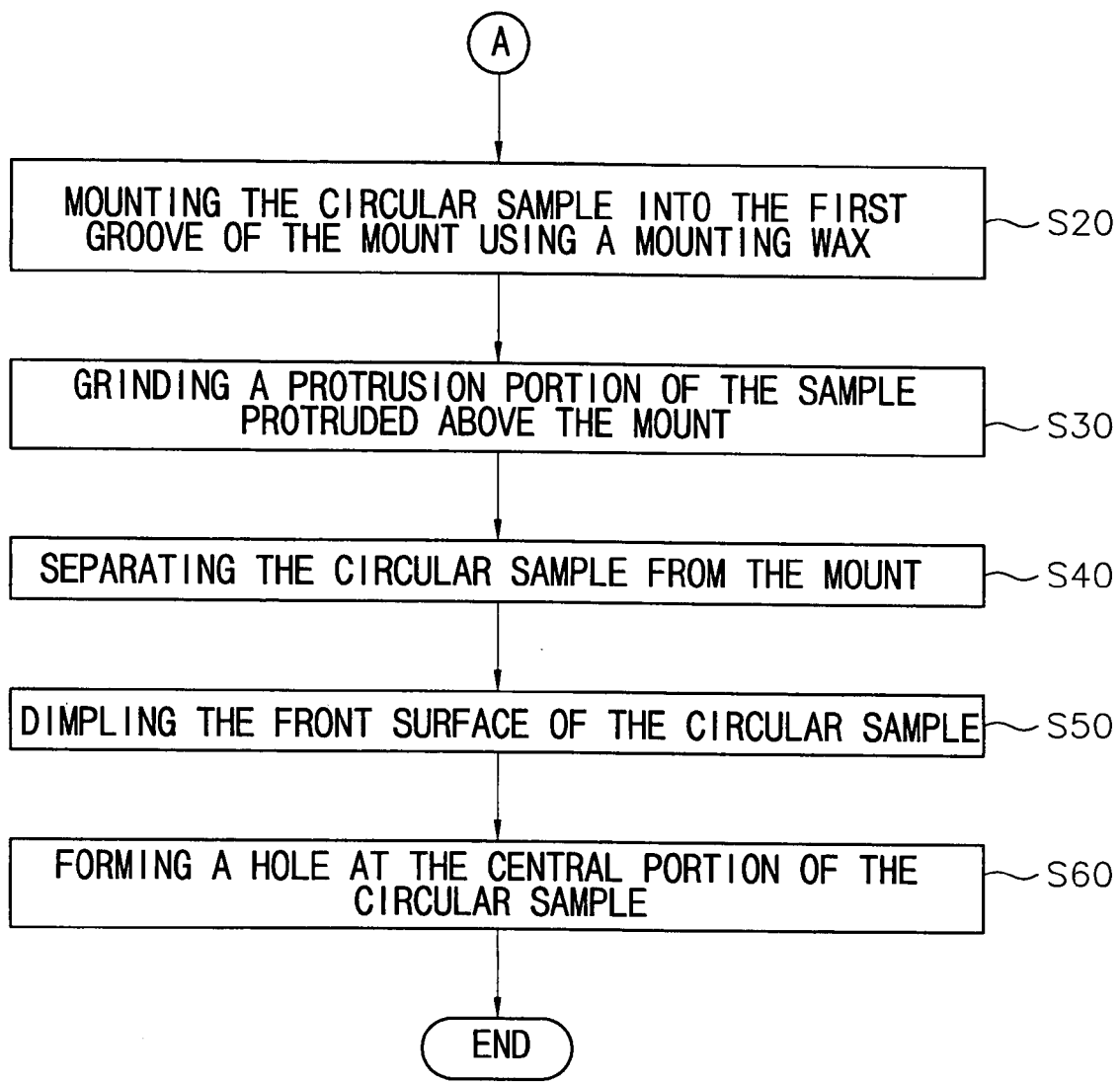
Figure 6:
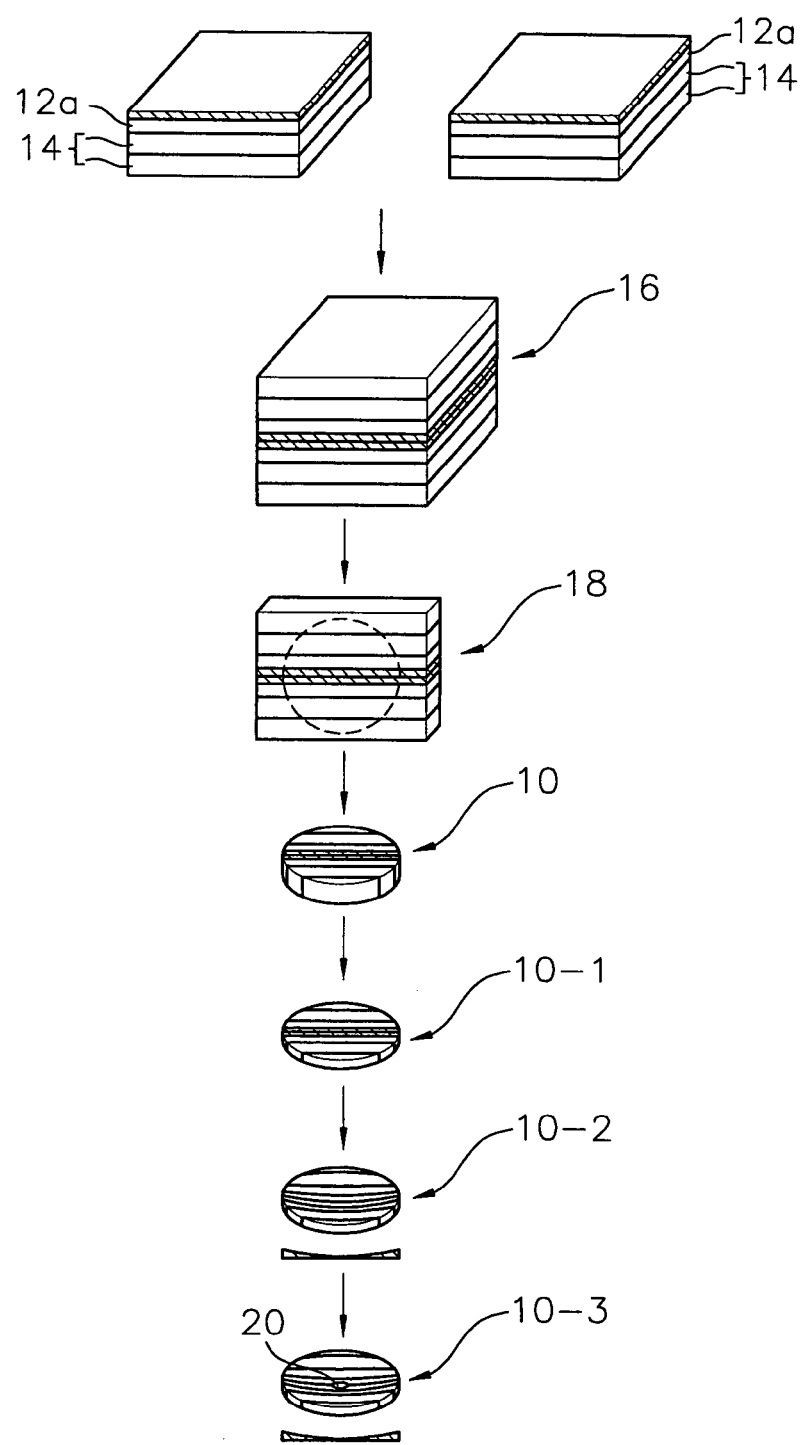
FIG. 6 is a perspective view illustrating a sample manufactured by the method illustrated in FIGS. 5A and 5B.

FIGS. 5A and 5B are flow charts illustrating a method of manufacturing a transmission electron microscope inspection sample using the mount shown in FIG. 1. FIG. 6 is a perspective view illustrating a sample manufactured by the method illustrated in FIGS. 5A and 5B.

Referring to FIGS. 1, 2, 5A, 5B and 6, a method of manufacturing the sample includes the following: Preparing the sample 10 (step S10). Mounting the sample 10 into the mount 100 (step S20). Grinding the protruding portion of the sample 10 that protrudes above the top surface 100*a* of the mount 100 (step S30). Separating the sample 10 from the mount 100 (step S40). Dimpling the sample 10 (step S50). Forming a hole at a central portion of the dimpled sample 10 (step S60).

The preparing of the sample 10 (step S10) includes a plurality of steps, as denoted by the reference numerals S102 through S114 in FIG. 5A. In step S102, a first silicon wafer 12*a* and a second silicon wafer 12*b* are obtained from an arbitrary silicon wafer including a layer or a pattern with a predetermined size. For example, the first silicon wafer 12*a* may have a thickness of about 4 mm and a length of about 5 mm. The second silicon wafer 12*b* may have the same size as that of the first silicon wafer 12*a*.

In step S104, at least one dummy wafer 14 is adhered to both rear surfaces of the first and second silicon wafers 12*a* and 12*b*, respectively. In embodiments, the first and second silicon wafers 12*a* and 12*b* are the same size as that of the dummy wafers 14. In step S106, the first silicon wafer 12*a* and the second silicon wafer 12*b* are adhered to each other such that the front surface of the first silicon wafer 12*a* faces the front surface of the second silicon wafer 12*b*, forming a sample stack 16.

In step S108, the sample stack 16 is sliced into pieces (e.g. using a diamond saw) so that cross-sectional surfaces of the first and second silicon wafers 12*a* and 12*b* are exposed to form a preliminary sample 18. For example, the sample stack 16 is sliced along a cutting direction perpendicular to the front surfaces of the first and second silicon wafers 12*a* and 12*b*. The preliminary sample 18 has a width of about 4 mm, a length of about 5 mm, and a thickness of about 1000 μm.

In step S110, the preliminary sample 18 is then cut into a disk shape to form the sample 10 having a circular shape. For example, the sample 10 may have a circular shape with a diameter of about 3 mm. In step S112, the front surface 10*a* of the circular sample 10 is grinded. The front surface 10*a* of the sample 10 is perpendicular to the front surfaces of the first and second silicon wafers 12*a* and 12*b*. After grinding, the front surface of the sample 10 is polished such that the sample 10 has a thickness of about 400 μm.

In step S20, mounting wax is coated on inner surfaces of the recess 102 of the mount 100 and the polished sample 10 is mounted into the recess 102 of the mount 100, such that the polished front surface 10*a* of the circular sample 10 faces the bottom surface 102*a* of the recess 102.

In step S30, the protruding portion 10*c* of the sample 10 is grinded. The protruding portion 10*c* protrudes above the top surface 100*a* of the mount 100. The sample 10 is grinded by a plurality of disk grinders (not shown). Each of the disk grinders may have different grinding paper. For example, a silicon carbide paper having a diameter of about 40 μm, 15 μm, or 5 μm may be sequentially installed to each of the disk grinders. The sample 10 is grinded to the top surface 100*a* of the mount 100. In other words, the sample 10 is sequentially grinded by the disk grinders such that the rear surface 10*b* of the sample 10 mounted into the recess 102 is aligned with the top surface 100*a* of the mount 100. Therefore, the grinded sample 10-1 may have a thickness of about 70 µm.

In step S40, the grinded sample 10-1 is separated from the mount 100. The mounting wax interposed between the grinded sample 10-1 and the recess 102 of the mount 100 may be heated to a temperature of about 100° C., thus adhesion force of the mounting wax is weakened. Subsequently, the grinded sample 10-1 is separated from the mount 100 using the groove 104 of the mount 100.

In step S50, the dimpling process is performed on the front surface 10*a* of the grinded sample 10-1 using a dimpler (not shown). In step S60, a hole is formed at a central portion of the dimpled sample 10-2 using an ion miller (not shown) to form a sample for inspection by a transmission electron microscope.

According to embodiments of the present invention, a transmission electron microscope inspection sample is mounted into a recess of the mount using mounting wax and is grinded by a disk grinder to a predetermined target thickness. Therefore, the sample is prevented from being broken during the grinding and may be grinded to a target thickness.

Although example embodiments of the present invention have been described, it is understood that the present invention should not be limited to these example embodiments. Various changes and modifications can be made by one skilled in the art within the spirit and scope of the present invention as hereinafter claimed.

What is claimed is:

1. A grinding mount for receiving a transmission electron microscope (TEM) inspection sample to be grinded, the sample having a given thickness and a given outer profile, comprising:
a rigid body having a principle surface;
a recess defined in the principle surface of the rigid body, wherein a horizontal profile of the recess corresponds to the given outer profile of the sample and wherein a vertical depth of the recess is less than the given thickness of the sample; and
a groove defined in the principle surface of the rigid body, wherein the groove partially overlaps the recess and wherein a vertical depth of the groove is greater than the vertical depth of the recess.

2. The grinding mount of claim 1, wherein the sample has second given thickness after a grinding process, and wherein the second given thickness is less than the depth of the recess by about 1 µm to about 10 µm.

3. The grinding mount of claim 1, wherein the horizontal profile of the recess is circular.

4. The grinding mount of claim 3, wherein the recess has a diameter in a range of about 3.05 mm to about 3.15 mm and has a depth in a range of about 71 µm to about 80 µm.

5. The grinding mount of claim 3, wherein the groove extends from approximately the center of the recess in a radial direction of the recess.

6. The grinding mount of claim 5, wherein the groove has a width smaller than the radius of the recess, a length longer than the radius of the recess, and a depth in a range of about 80 µm to about 90 µm.

7. The mount of claim 3, wherein the groove extends over a diameter of the recess.

8. The grinding mount of claim 7, wherein the groove has a width smaller than the radius of the recess, a length longer than the diameter of the recess, and a depth in a range of about 80 µm to about 90 µm.

9. The grinding mount of claim 1, wherein the mount has a cylindrical shape, and the recess and the groove are disposed on a top surface of the cylinder.

10. The mount of claim 9, wherein the sample is mounted to the recess using mounting wax.

11. A method of treating a transmission electron microscope inspection sample, comprising:
mounting the sample to a recess in a mount, wherein the shape of the recess corresponds to the shape of the sample;
grinding a protruding portion of the sample which protrudes from the mount; and
separating the sample from the mount.

12. The method of claim 11, wherein the depth of the recess is greater than a target thickness of the sample by a distance in a range of about 1 µm to about 10 µm.

13. The method of claim 12, wherein the sample has a disk shape and the ungrinded thickness of the sample is greater than the depth of the recess.

14. The method of claim 13, further comprising preparing the sample, wherein the preparing the sample comprises:
adhering at least one first dummy wafer to a rear surface of a first silicon wafer;
adhering at least one second dummy wafer to a rear surface of a second silicon wafer;
adhering the first and second silicon wafers such that a front surface of the first silicon wafer faces a front surface of the second silicon wafer;
slicing the first and second silicon wafers to form a preliminary sample having a plate shape; and
cutting the preliminary sample into the disk shape of the sample.

15. The method of claim 14, wherein:
the grinding the protruding portion of the sample comprises grinding a front surface of the sample;
the front surface of the sample is perpendicular to the front surfaces of the first and second silicon wafers; and
the method comprises polishing the front surface of the sample.

16. The method of claim 15, wherein the sample is fixed to the mount using mounting wax such that the polished front surface of the sample faces a bottom surface of the groove.

17. The method of claim 16, further comprising separating the sample from the groove using acetone.

18. The method of claim 11, wherein the protruding portion of the sample is grinded to be aligned with the top surface of the mount.

19. The method of claim 11, further comprising:
dimpling the front surface of the sample separated from the mount; and
forming a hole at a center portion of the sample.

* * * * *